(12) United States Patent
Kelley

(10) Patent No.: US 11,648,042 B2
(45) Date of Patent: May 16, 2023

(54) PROCESSES AND METHODS FOR CONDUCTIVE ELEMENTS ON CATHETER ELEMENTS USED FOR TISSUE SENSING AND CRYOGENIC ABLATION

(71) Applicant: Medtronic CryoCath LP, Toronto (CA)

(72) Inventor: Jay L. Kelley, Encinitas, CA (US)

(73) Assignee: Medtronic CryoCath LP, Toronto (CA)

(*) Notice: Subject to any disclaimer, the term of this patent is extended or adjusted under 35 U.S.C. 154(b) by 1503 days.

(21) Appl. No.: 15/888,589

(22) Filed: Feb. 5, 2018

(65) Prior Publication Data

US 2018/0221077 A1 Aug. 9, 2018

Related U.S. Application Data

(60) Provisional application No. 62/455,182, filed on Feb. 6, 2017.

(51) Int. Cl.
*A61M 25/10* (2013.01)
*A61B 18/02* (2006.01)
(Continued)

(52) U.S. Cl.
CPC ............ *A61B 18/02* (2013.01); *A61L 29/02* (2013.01); *A61L 29/041* (2013.01); *A61L 29/06* (2013.01);
(Continued)

(58) Field of Classification Search
CPC .......... A61M 25/1029; A61M 25/1027; A61M 2025/1031; A61B 18/02; A61B 2017/00526; A61B 2018/00077; A61B 2018/0022; A61B 2018/00375; A61B 2018/00577; A61B 2018/00839; A61B 2018/00875; A61B 2018/0212; A61L 29/02; A61L 29/041; A61L 29/06; A61L 29/126; A61L 29/14; A61L 2400/12; B29C 48/022; B29C 49/0005; B29C 48/0017; B29C 48/09; B29C 48/155; B29C 48/156;
(Continued)

(56) References Cited

U.S. PATENT DOCUMENTS

2002/0087156 A1\* 7/2002 Maguire ............ A61B 18/1492
606/41
2007/0219576 A1\* 9/2007 Cangialosi ............ A61M 29/02
606/198

OTHER PUBLICATIONS

Saifuddin, et al., "Carbon Nanotubes: A Review on Structure and Their Interaction with Proteins", Journal of Chemistry, vol. 13, 18 pages. (Year: 2012).\*

\* cited by examiner

*Primary Examiner* — Amber R Stiles
(74) *Attorney, Agent, or Firm* — Michael Best & Friedrich LLP

(57) ABSTRACT

A method, system and device for securing conductive material on catheter elements for tissue sensing and cryogenic ablation. This may be used to deposit or embed conductive material onto or within polymeric materials. The method of manufacturing a balloon with conductive material may include extruding a polymeric material where the polymeric material includes embedded electrically conductive material. At least a portion of the polymeric material may be removed to expose at least a portion of the embedded electrically conductive material. The benefits may include allowing local bipolar recordings, contact assessment and ice thickness, and compatibility with 3-dimensional electro-anatomical mapping systems.

13 Claims, 12 Drawing Sheets

(51) Int. Cl.
*B29C 49/00* (2006.01)
*A61L 29/06* (2006.01)
*A61L 29/04* (2006.01)
*A61L 29/02* (2006.01)
*A61L 29/14* (2006.01)
*B29C 48/00* (2019.01)
*A61L 29/12* (2006.01)
*B29L 31/00* (2006.01)
*A61B 18/00* (2006.01)
*B29C 49/04* (2006.01)
*B29K 101/12* (2006.01)
*B29K 505/14* (2006.01)
*B29K 507/04* (2006.01)
*B29K 105/16* (2006.01)
*B29C 48/09* (2019.01)
*A61B 17/00* (2006.01)
*B29C 48/155* (2019.01)
*B29L 31/34* (2006.01)
*B29C 48/156* (2019.01)

(52) U.S. Cl.
CPC .............. *A61L 29/126* (2013.01); *A61L 29/14* (2013.01); *A61M 25/1029* (2013.01); *B29C 48/022* (2019.02); *B29C 49/0005* (2013.01); *A61B 2017/00526* (2013.01); *A61B 2018/0022* (2013.01); *A61B 2018/00077* (2013.01); *A61B 2018/00375* (2013.01); *A61B 2018/00577* (2013.01); *A61B 2018/00839* (2013.01); *A61B 2018/00875* (2013.01); *A61B 2018/0212* (2013.01); *A61L 2400/12* (2013.01); *A61M 2025/1031* (2013.01); *B29C 48/0017* (2019.02); *B29C 48/09* (2019.02); *B29C 48/155* (2019.02); *B29C 48/156* (2019.02); *B29C 49/04* (2013.01); *B29K 2101/12* (2013.01); *B29K 2105/162* (2013.01); *B29K 2505/14* (2013.01); *B29K 2507/04* (2013.01); *B29K 2995/0005* (2013.01); *B29L 2031/3462* (2013.01); *B29L 2031/7543* (2013.01)

(58) Field of Classification Search
CPC ................ B29C 49/04; B29K 2101/12; B29K 2105/162; B29K 2505/14; B29K 2507/04; B29K 2995/0005; B29L 2031/3462; B29L 2031/7543
See application file for complete search history.

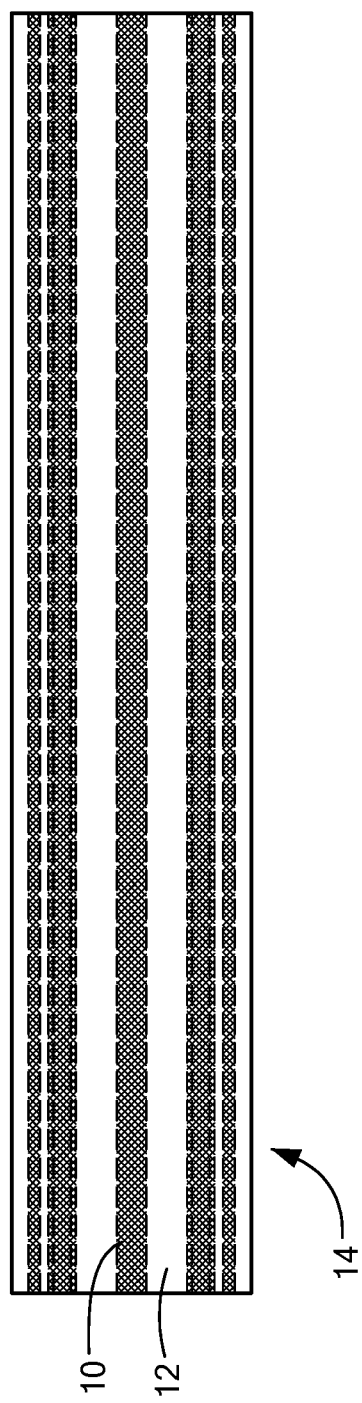
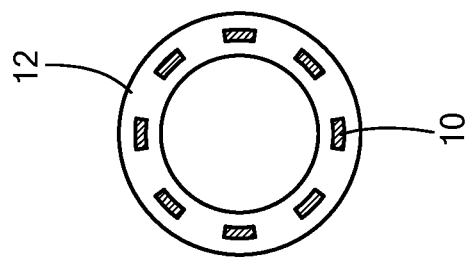
FIG. 1
FIG. 2

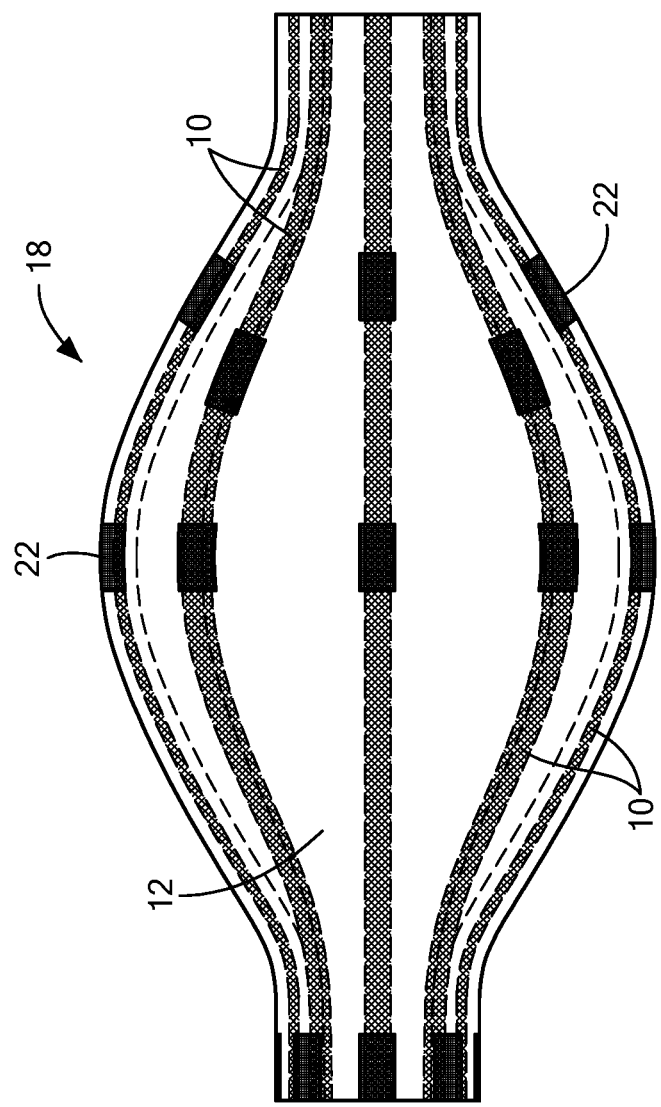
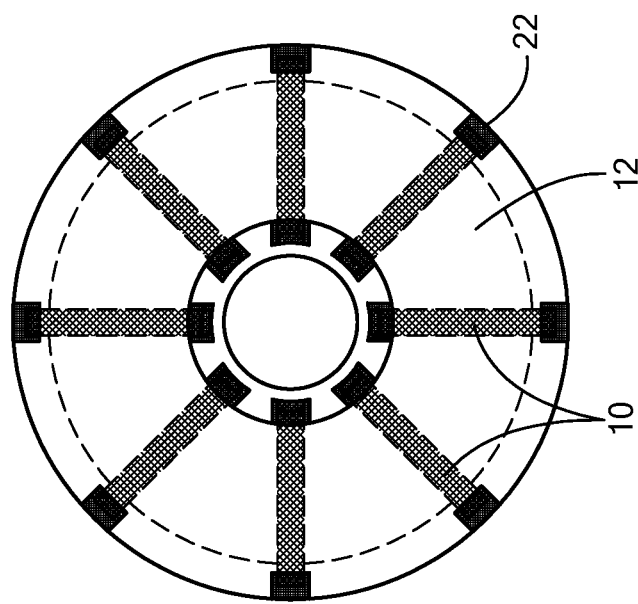
FIG. 7
FIG. 8

PROCESSES AND METHODS FOR CONDUCTIVE ELEMENTS ON CATHETER ELEMENTS USED FOR TISSUE SENSING AND CRYOGENIC ABLATION

CROSS-REFERENCE TO RELATED APPLICATION

This application is related to and claims priority to U.S. Provisional Patent Application Ser. No. 62/455,182, filed Feb. 6, 2017, entitled PROCESSES AND METHODS FOR CONDUCTIVE ELEMENTS ON CATHETER ELEMENTS USED FOR TISSUE SENSING AND CRYOGENIC ABALATION, the entirety of which is incorporated herein by reference.

STATEMENT REGARDING FEDERALLY SPONSORED RESEARCH OR DEVELOPMENT n/a

TECHNICAL FIELD

The present invention relates to endovascular catheters. In particular, the present invention relates to a method and system for securing electrically conductive elements on catheter elements for tissue sensing and cryogenic ablation as well as a medical device with electrically conductive elements on catheter elements.

BACKGROUND

Minimally invasive devices, such as catheters, are often employed for surgical procedures, including those involving sensing, ablation, dilation, as well as other procedures. In certain situations, a physician may use a catheter having variations in the geometry and/or dimensions of the ablative element in order to produce the desired ablation pattern. Each catheter may have a unique geometry for creating a specific lesion pattern.

Applying these sensing and/or ablative elements onto the catheter is very challenging and can sometimes increase the risk to the patient undergoing treatment with the device when there are issues with the sensing and/or ablative element. For example, when sensing and/or ablative elements are attached to a portion of the catheter, the sensing and/or ablative elements are often not secure and can come off the device. This can put the patient at significant risk when these elements come off the device while the device is being used in tissue. Additionally, when the sensing and/or ablative element is secured to a balloon on a catheter, when the balloon is expanded the sensing and/or ablative element may be deformed or it may damage the balloon. When this occurs with a sensing and/or ablative element, it can be dangerous for the patient undergoing the treatment. Accordingly, it would be desirable to have a method that can deposit or embed electrically conductive material onto or within polymeric materials that reliably secures the electrically conductive elements onto the catheter.

SUMMARY

The present invention advantageously provides devices having electrically conductive elements, such as balloons with electrically conductive elements, and methods and systems for manufacturing same. In one embodiment, a method of manufacturing a balloon with electrically conductive material comprises extruding a polymeric material, the polymeric material including embedded electrically conductive material; and removing at least a portion of the polymeric material to expose at least a portion of the embedded electrically conductive material.

In one aspect of the embodiment, the polymeric material is at least one of a group consisting of a thermoplastic polyurethane, a thermoplastic elastomer, a polyamide, an ethylene vinyl acetate, a polyvinylidene fluoride, and a polyvinyl chloride.

In one aspect of the embodiment, the electrically conductive material is an embedded first electrically conductive material, the method further comprising electroplating the exposed at least a portion of the embedded first electrically conductive material with a second electrically conductive material.

In one aspect of the embodiment, the embedded first electrically conductive material is a conductive ink and the second electrically conductive material is gold.

In one aspect of the embodiment, the extruded polymeric material has a tubular first configuration, the method further comprising: expanding the polymeric material into an expanded second configuration.

In one aspect of the embodiment, at least a portion of the polymeric material is removed to expose at least a portion of the embedded electrically conductive material after the polymeric material is expanded into the expanded second configuration.

In one aspect of the embodiment, the electrically conductive material is a temperature-activated material, the method further comprising: heating the electrically conductive material, the conductive material becoming conductive when heated.

In one aspect of the embodiment, the electrically conductive material includes flakes of electrically conductive material.

In one aspect of the embodiment, the electrically conductive material includes nanotubes.

In one aspect of the embodiment, the nanotubes are at least one of a single wall carbon nanotube and a single wall graphene nanotube.

In one aspect of the embodiment, the electrically conductive material includes at least one nanowire.

In one aspect of the embodiment, the at least one nanowire includes at least one silver nanowire.

In one aspect of the embodiment, the embedded electrically conductive material is supersonically implanted into the polymeric material as the polymeric material is extruded.

In another embodiment, a method for manufacturing a balloon with electrically conductive material comprises: extruding a polymeric material into a tubular first configuration; depositing an electrically conductive material onto at least a portion of the polymeric material; and depositing a dielectric material onto at least a portion of the electrically conductive material.

In one aspect of the embodiment, the dielectric material is deposited onto an entirety of the electrically conductive material, the method further comprising: expanding the polymeric material into an expanded second configuration; and removing at least a portion of the dielectric material to expose at least a portion of the electrically conductive material.

In one aspect of the embodiment, the dielectric material is deposited onto the electrically conductive material such that at least a portion of the electrically conductive material is exposed, the electrically conductive material being a first electrically conductive material, the method further comprising: electroplating the exposed electrically conductive material with a second electrically conductive material.

In yet another embodiment, a medical device comprises: a balloon composed of an insulative polymeric material with an electrically conductive element embedded therein, the balloon including an outer surface; and an elongate body having a proximal portion and a distal portion, the balloon being coupled to the distal portion. At least a portion of the insulative polymeric material is removed from the balloon outer surface to expose at least a portion of the embedded electrically conductive element.

In one aspect of the embodiment, the embedded electrically conductive element is an embedded first electrically conductive material, the exposed at least a portion of the embedded first electrically conductive element having an electroplated layer of a second electrically conductive element.

In one aspect of the embodiment, the embedded electrically conductive element includes graphene nanotubes.

In one aspect of the embodiment, the embedded electrically conductive element includes gold particles that have been supersonically implanted into the polymeric material.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein:

FIG. 1 shows a first step of a first exemplary method of forming a balloon for a medical device, in which polymeric material is extruded and includes embedded electrically conductive material;

FIG. 2 shows a cross-sectional view of the polymeric material of FIG. 1;

FIG. 7 shows an optional fourth step of the first exemplary method of forming the balloon, in which the exposed embedded electrically conductive material is electroplated;

FIG. 8 shows a cross-sectional view of the polymeric material of FIG. 7;

DETAILED DESCRIPTION

Figure 3:
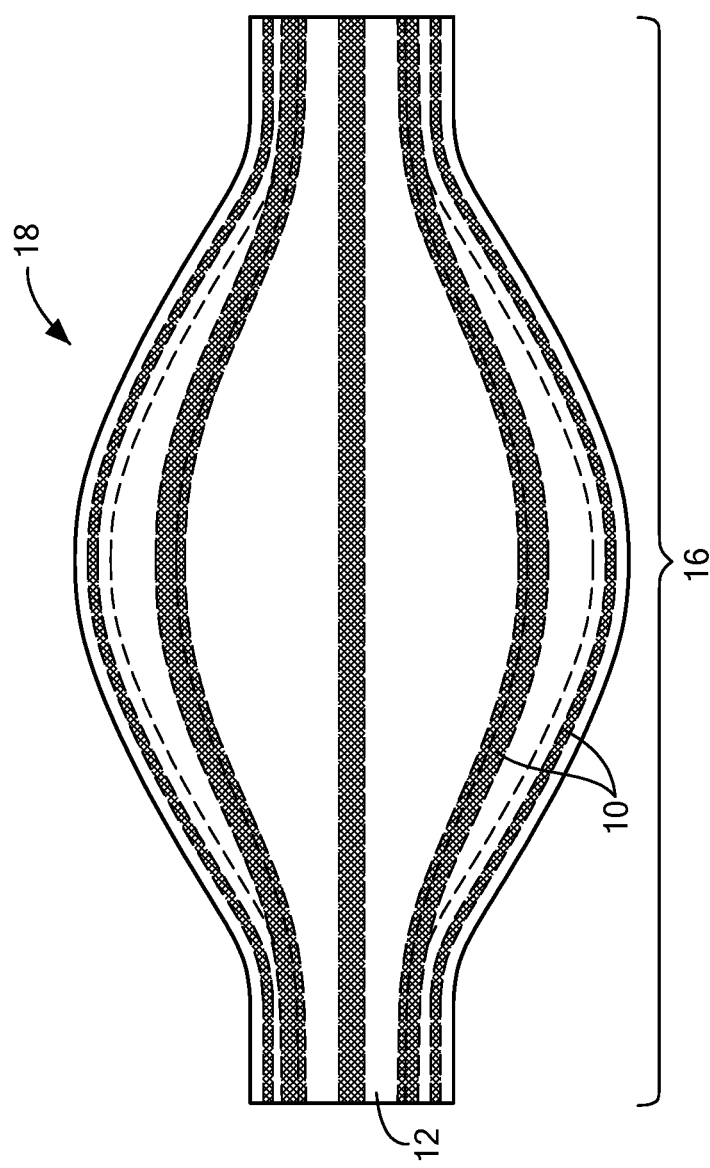
FIG. 3 shows a second step of the first exemplary method of forming the balloon, in which the polymeric material of FIG. 1 is expanded.

Before describing in detail exemplary embodiments that are in accordance with the disclosure, it is noted that the embodiments reside primarily in combinations of apparatus components and processing steps related to a method and system for securing electrically conductive material on catheter elements for tissue sensing and cryogenic ablation. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Many currently known balloons used for performing medical procedures (for example, cryoballoons used for pulmonary vein isolation) do not include electrically conductive elements (electrodes). However, including electrically conductive elements on a balloon has numerous benefits. For example, the presence of electrically conductive elements on a balloon enables the balloon to be used for recording local bipolar signals, such as local bipolar electrograms, from adjacent tissue. Additionally, the electrically conductive elements may be used to record impedance measurements from adjacent tissue for balloon-tissue contact assessment and evaluation of ice ball thickness during a cryoablation procedure. Both of these characteristics may be used to evaluate or predict the effectiveness of a cryoablation procedure. Further, the electrically conductive elements may be compatible with 3-dimensional eletroanatomical mapping systems via an impedance mapping.

Referring now to the drawings in which like reference designators refer to like elements, several methods for creating a balloon with electrically conductive elements are shown, as well as an exemplary embodiment of a medical device including a balloon with electrically conductive elements. Referring now to FIGS. 1-10, a first exemplary method is shown. In this method, the polymeric material includes electrically conductive material 10 embedded within the polymeric material 12, and the electrically conductive material 10 is exposed to create discrete electrically conductive elements on the finished balloon. In a first step, as shown in FIGS. 1 and 2, a polymeric material 12 may be extruded with the electrically conductive material 10 such that the polymeric material 12 includes embedded electrically conductive material 10. When the polymeric material 12 and electrically conductive material 10 are extruded, they may be co-extruded or alternatively one material may be extruded and then the second material may be extruded. Additionally or alternatively, the electrically conductive material 10 may be supersonically implanted into the polymeric material 12 as the polymeric material 12 is extruded. After the polymeric material 12 and electrically conductive material 10 are extruded, they may have a first configuration with a tubular shape 14. When extruding the polymeric material 12 and electrically conductive material 10, various other shapes may also be created which includes, but is not limited to a rectangular, square, and oval shape. The determination of what shape to use may depend upon how and where the material is going to be used. Co-extruding the polymeric material 12 and the electrically conductive material 10 may produce a uniform extrudate or uniform printing. The electrically conductive material 10 may be entirely embedded within the polymeric material 12 such that the polymeric material 12 entirely surrounds the electrically conductive material 10. Alternatively, only a portion of the electrically conductive material 10 may be embedded within the polymeric material 12 or the electrically conductive material 10 may be entirely or partially on the outer surface of the polymeric material 12.

When the polymeric material 12 and the electrically conductive material 10 are extruded, micro-cracks may form when the electrically conductive material 10 is embedded within the polymeric material 12. These micro-cracks allow conductivity while undergoing strain and movement. The embedded electrically conductive material 10 may be supersonically implanted into the polymeric material 12 as the polymeric material 12 is extruded. In one exemplary embodiment, gold particles may be supersonically implanted into the polymeric material 12 as polymeric material 12 and electrically conductive material 10 are extruded, which allows for the placement of the electrically conductive material 10 at a desired depth within the polymeric material 12. Alternatively, electrically conductive material 10 may be deposited on the polymeric material 12 and secondary processing may be used to control microcrack formation.

The polymeric material may include at least one from the group consisting of thermoplastic polyurethanes, thermoplastic elastomers, polyamides, ethylene vinyl acetates, polyvinylidene fluoride, and polyvinyl chloride. The electrically conductive material 10 may include a flexible and stretchable polymer, and the flexible and stretchable polymer may be impregnated with electrically conductive elements, such as flakes of electrically conductive material, nanowires, and/or nanotubes. In one embodiment, the nanowires may be silver nanowires. In another embodiment, the nanotubes may be single wall carbon nanotubes or single wall graphene nanotubes. Additionally or alternatively, the electrically conductive material 10 may include conductive inks. More than one electrically conductive material 10 may be used together or just one electronically conductive material 10 may be used. As a non-limiting example, conductive ink and gold may be used together such that there is a primary and a secondary electrically conductive material 10. In other embodiments, more than two electrically conductive materials 10 may be used together.

Figure 4:
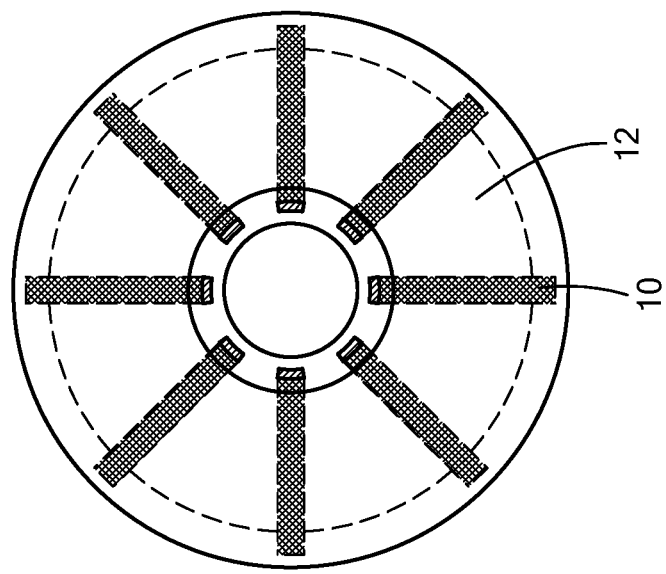
FIG. 4 shows a cross-sectional view of the polymeric material of FIG. 3.

In a second step, as shown in FIGS. 3 and 4, a length 16 of the electrically conductive material 10 with the polymeric material 12 may be extracted to a desired pre-formed length. The electrically conductive material 10 with the polymeric material 12 may also be molded, inflated and/or expanded to a desired shape. In one embodiment, the extruded polymeric material 12 may have the tubular first configuration 14 and then the polymeric material 12 may be inflated or expanded into an expanded second configuration 18. A solid, liquid, or a gas may be used to inflate or expand the polymeric material 12, which includes blow molding the polymeric material 12 into a desired shape. The type of electrically conductive material 10 that is used may be able to withstand the strain and temperature changes associated with the inflation/expansion process and may also be temperature-activated material and therefore become conductive upon heating. The temperature changes may also help the electrically conductive material 10 adhere to the polymeric material 12.

Figure 5:
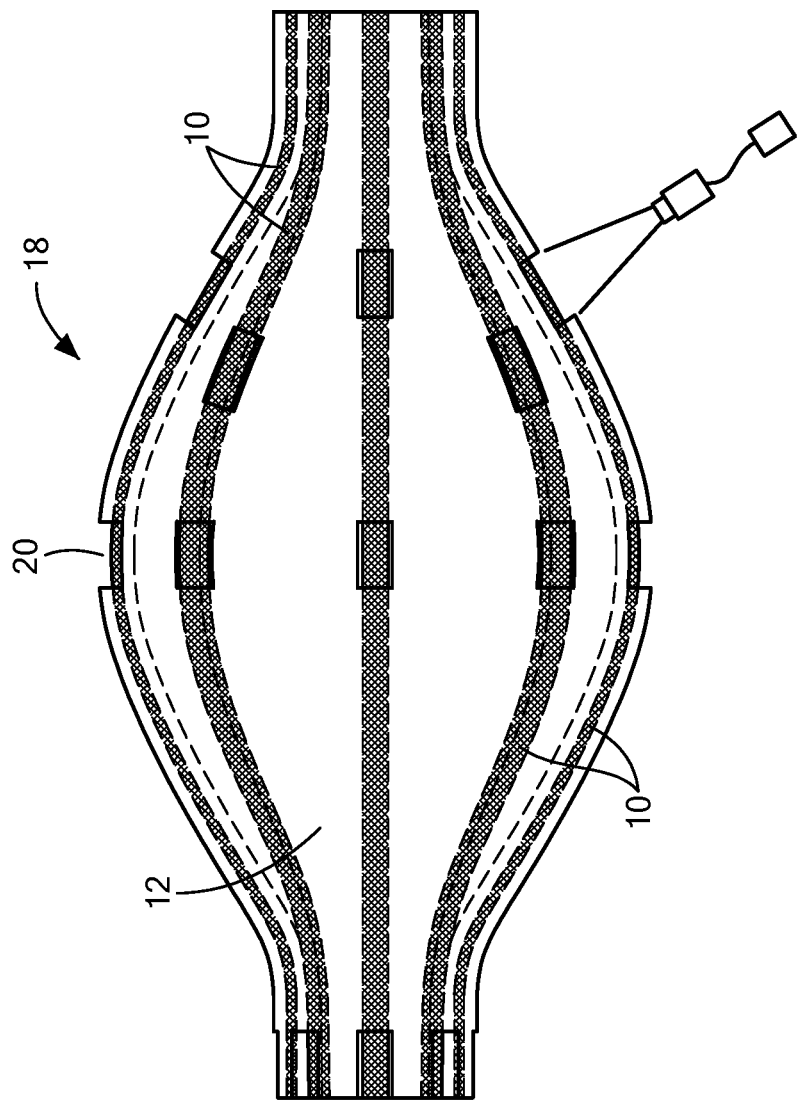
FIG. 5 shows a third step of the first exemplary method of forming the balloon, in which at least a portion of the polymeric material is removed to expose at least a portion of the embedded electrically conductive material.
Figure 6:
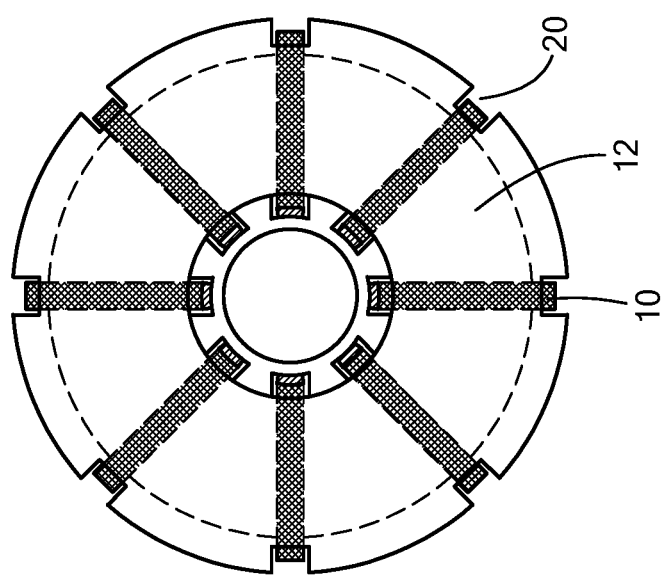
FIG. 6 shows a cross-sectional view of the polymeric material of FIG. 5.

In a third step, as shown in FIGS. 5 and 6, at least a portion of the polymeric material 12 over the electrically conductive material 10 may be removed to expose at least a portion of the embedded electrically conductive material 10 after the polymeric material 12 is expanded into the expended second configuration 18. As a non-limiting example, one or more areas of the outer surface of the polymeric material 12 may be removed by laser ablation, thereby creating one or more discrete areas 20 where embedded electrically conductive material 10 is exposed. The removal process may be performed before or after the polymeric material 12 is expanded into the expanded second configuration 18. Specific electrically conductive material 10 may be targeted when removing the polymeric material 12.

In an optional fourth step, as shown in FIGS. 7 and 8, electroplating chemistry may be used to deposit metal 22 into the areas where the layer of polymeric material 12 has been removed and the electrically conductive material 10 is exposed. As a non-limiting example, a metal 22, such as gold, may be deposited using electroplating chemistry into the at least one discrete area 20. This optional electroporation step may enhance the mechanical and/or electrical performance of the electrically conductive material 10.

Figures 9, 10:
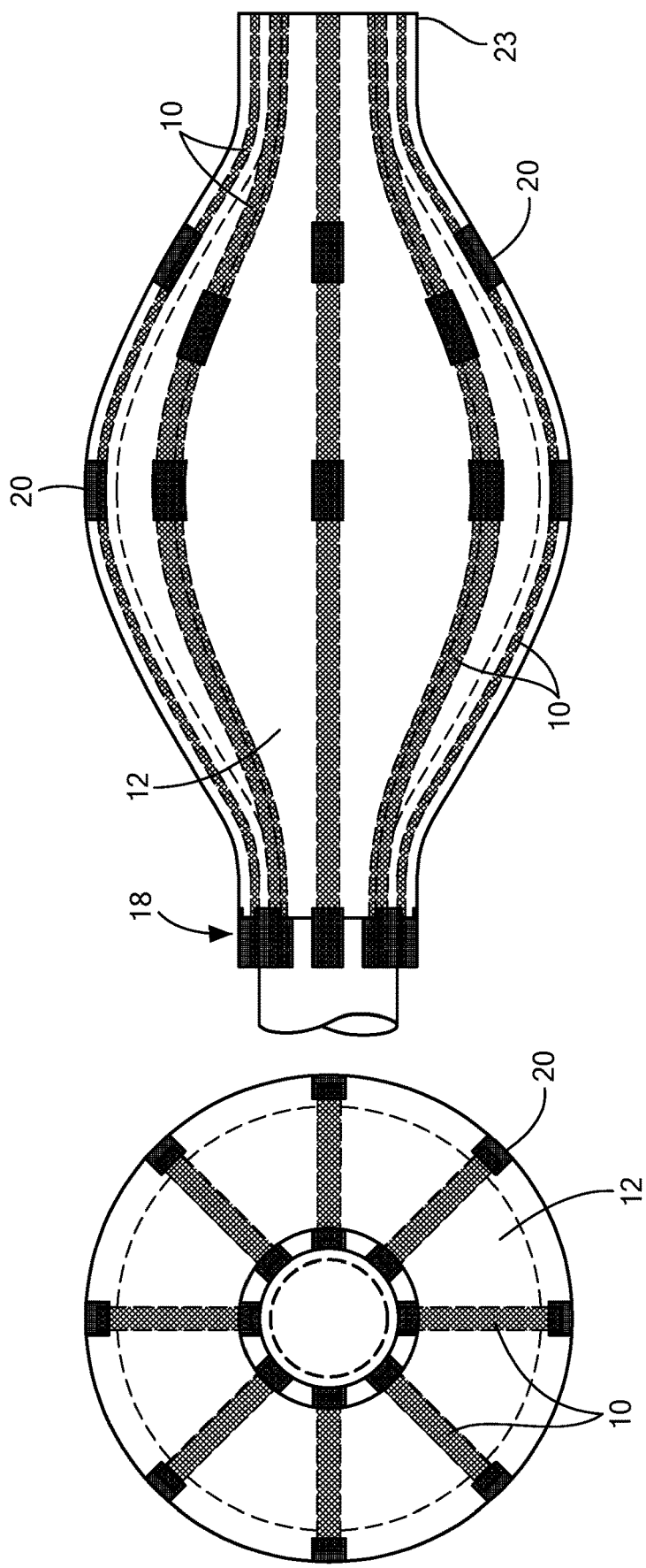
FIG. 9 shows a fifth step of the first exemplary method of forming the balloon, in which the polymeric material at the ends of the balloon is modified or removed to allow for electrical connection to other components of the medical device.
FIG. 10 shows a cross-sectional view of the polymeric material of FIG. 9.

In a fifth step, as shown in FIGS. 9 and 10, an outer layer of the polymeric material 12 may be removed in specific locations using a chemical or mechanical process to remove the polymeric material 12 as shown in FIG. 5. As a non-limiting example, a chemical or mechanical process may be used on the outer layer of the polymeric material 12 to remove at least a portion of the polymeric material 12 from the electrically conductive material 10. A mandrel 23 may be used to structurally support the polymeric material 12 and the electrically conductive material 10 during this process. This process may allow part of the catheter to access the electrically conductive material 10.

Figure 11:
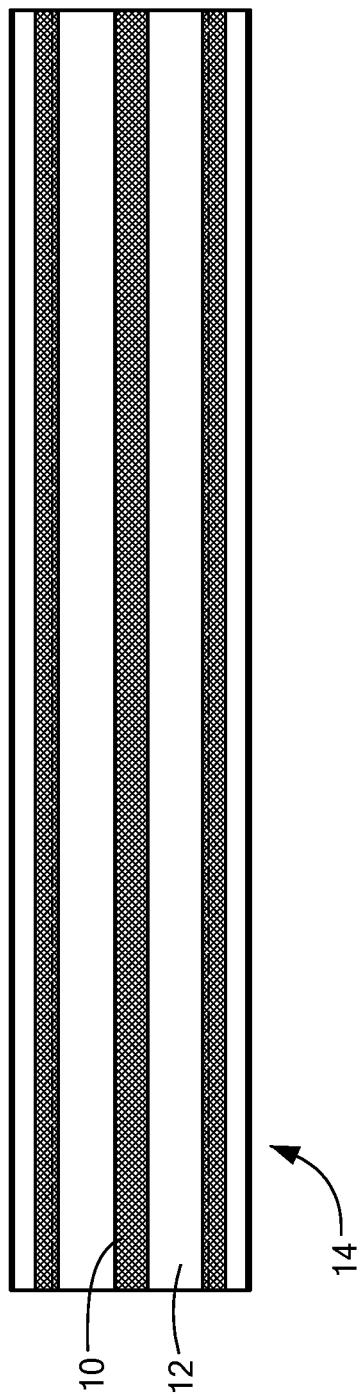
FIG. 11 shows a first step of a second exemplary method of forming a balloon for a medical device, in which polymeric material is extruded and electrically conductive material is deposited onto an outer surface of the extruded polymeric material and a layer of dielectric material is deposited onto at least a portion of the electrically conductive material.
Figure 12:
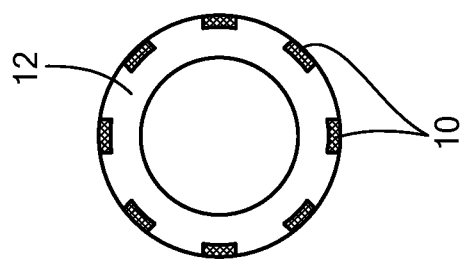
FIG. 12 shows a cross-sectional view of the polymeric material of FIG. 11.

Referring now to FIGS. 11-20, a second exemplary method is shown. In this method, the polymeric material 12 may be first extruded and then electrically conductive material 10 may be deposited onto an outer surface the polymeric material 12. One or more layers of a dielectric material may be deposited over all or at least a portion of the electrically conductive material 10. In a first step, as shown in FIGS. 11 and 12, the polymeric material 12 may be extruded into a tubular first configuration 14. The electrically conductive material 10 may be deposited onto at least a portion of the polymeric material 12. The electrically conductive material 10 may be deposited onto the polymeric material 12 while the polymeric material 12 is still warm as this may assist with adhesion and curing and may improve the mechanical and structural performance. Alternatively, electrically conductive material 10 may be deposited onto the polymeric material 12 after the polymeric material 12 has cooled down. A dielectric material may also be deposited onto only a portion of the electrically conductive material 10. The dielectric material may cover the electrically conductive material 10 in specific targeted locations or alternatively the dielectric material may be deposited onto the entirety of the electrically conductive material 10.

Figure 13:
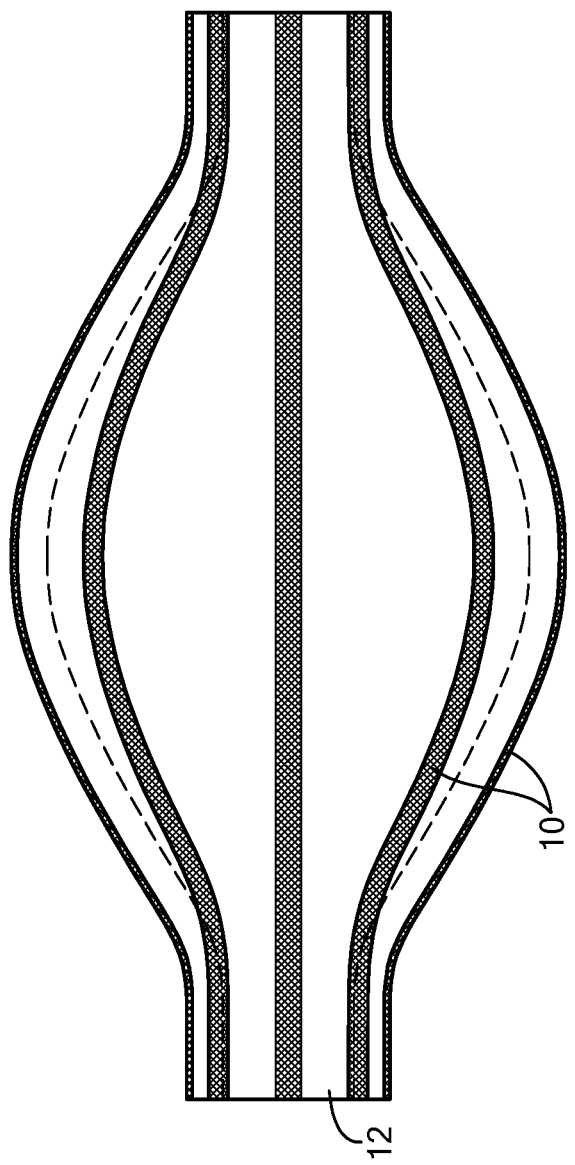
FIG. 13 shows a second step of the second exemplary method of forming the balloon, in which the polymeric material is expanded.
Figure 14:
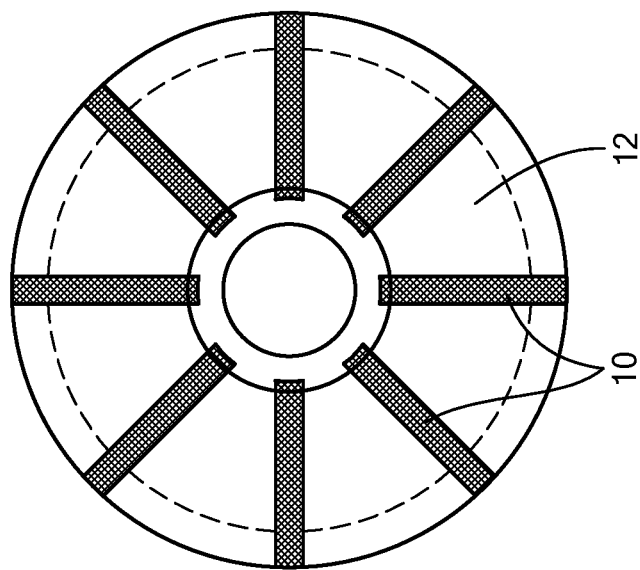
FIG. 14 shows a cross-sectional view of the polymeric material of FIG. 13.

In a second step, as shown in FIGS. 13 and 14, the electrically conductive material 10 and the polymeric material 12 may be inflated/expanded and/or molded into an expanded second configuration 18, which can be a desired shape and size. At least a portion of the dielectric material may be removed to expose at least a portion of the electrically conductive material 10. The electrically conductive material 10 and the polymeric material 12 may be temperature activated materials that become conductive upon heating.

Figure 15:
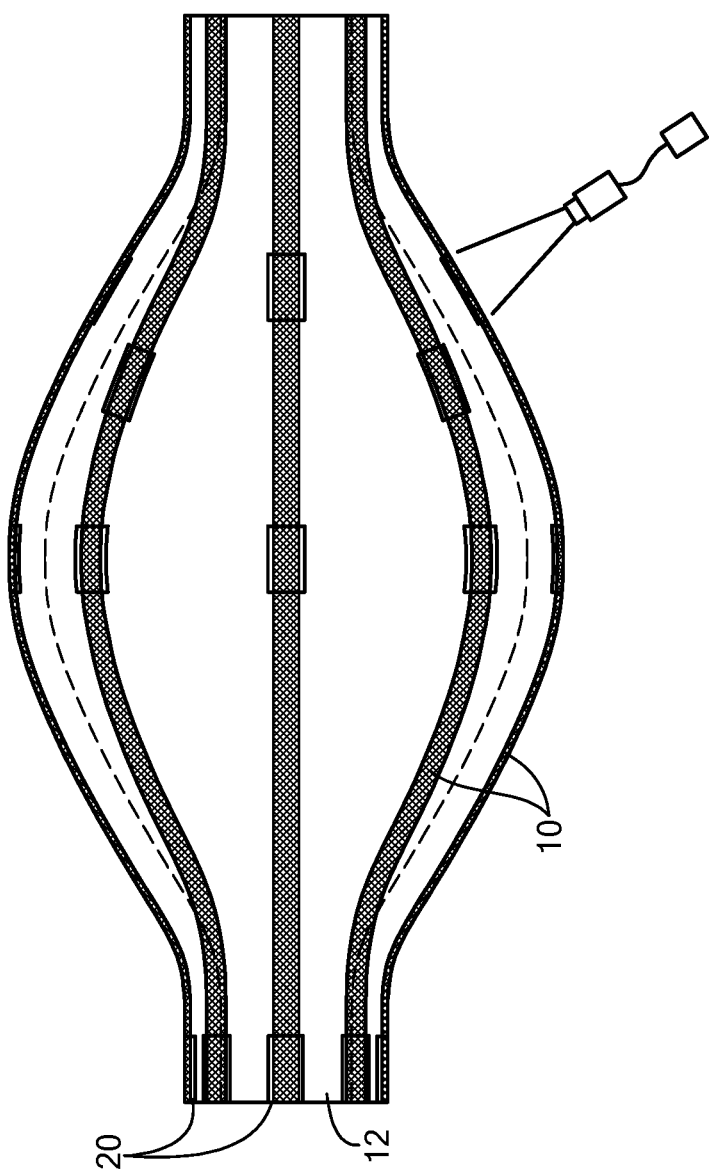
FIG. 15 shows an optional third step of the second exemplary method of forming the balloon, in which at least a portion of the layer of dielectric material is removed to expose at least a portion of the electrically conductive material.
Figure 16:
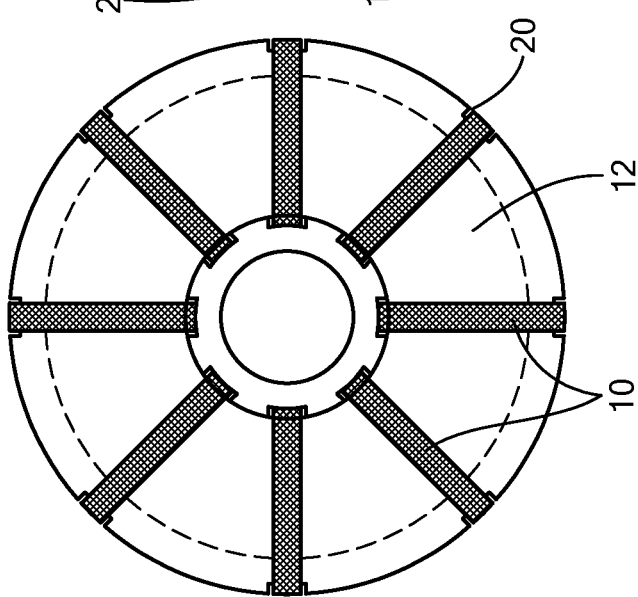
FIG. 16 shows a cross-sectional view of the polymeric material of FIG. 15.

As a third step, as shown in FIGS. 15 and 16, if the dielectric material is applied uniformly, the layer of the dielectric material may be removed at specific desired locations. As a non-limiting example, a layer of the polymeric material 12 may be ablated with a laser and the electrically conductive material 10 may be exposed in the discrete areas 20. This may be done before the inflation/expansion of the electrically conductive material 10 and the polymeric material 12 or after the inflation/expansion has occurred.

Figure 17:
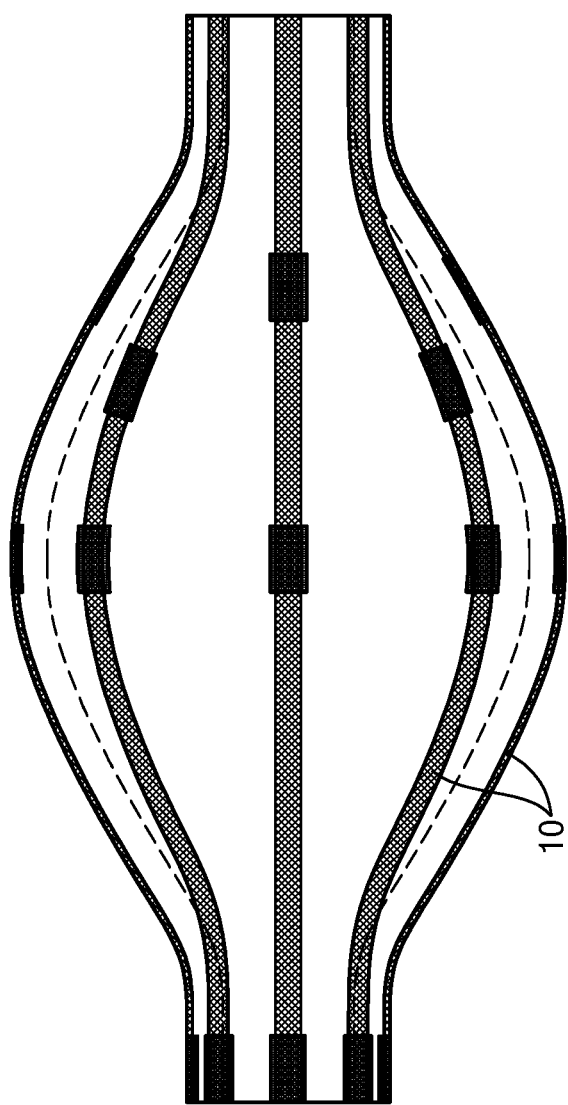
FIG. 17 shows an optional fourth step of the second exemplary method of forming the balloon, in which the exposed electrically conductive material is electroporated.
Figure 18:
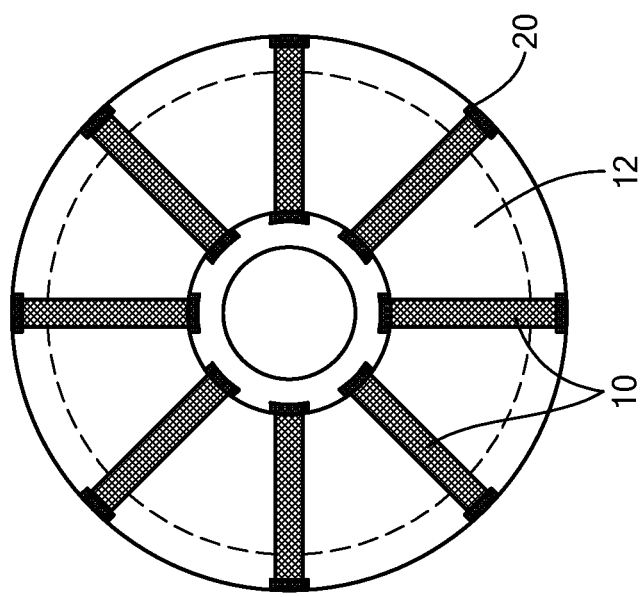
FIG. 18 shows a cross-sectional view of the polymeric material of FIG. 17.

In an optional fourth step, as shown in FIGS. 17 and 18, electroplating chemistry may be used to deposit a metal 22 into the areas where the layer of polymeric material 12 has been removed and the electrically conductive material 10 is exposed. As a non-limiting example, the electrically conductive material 10 may include a first electrically conductive material that may be electroplated where the electrically conductive material 10 has been exposed with a second electrically conductive material 10, for example with a metal 22.

Figures 19, 20:
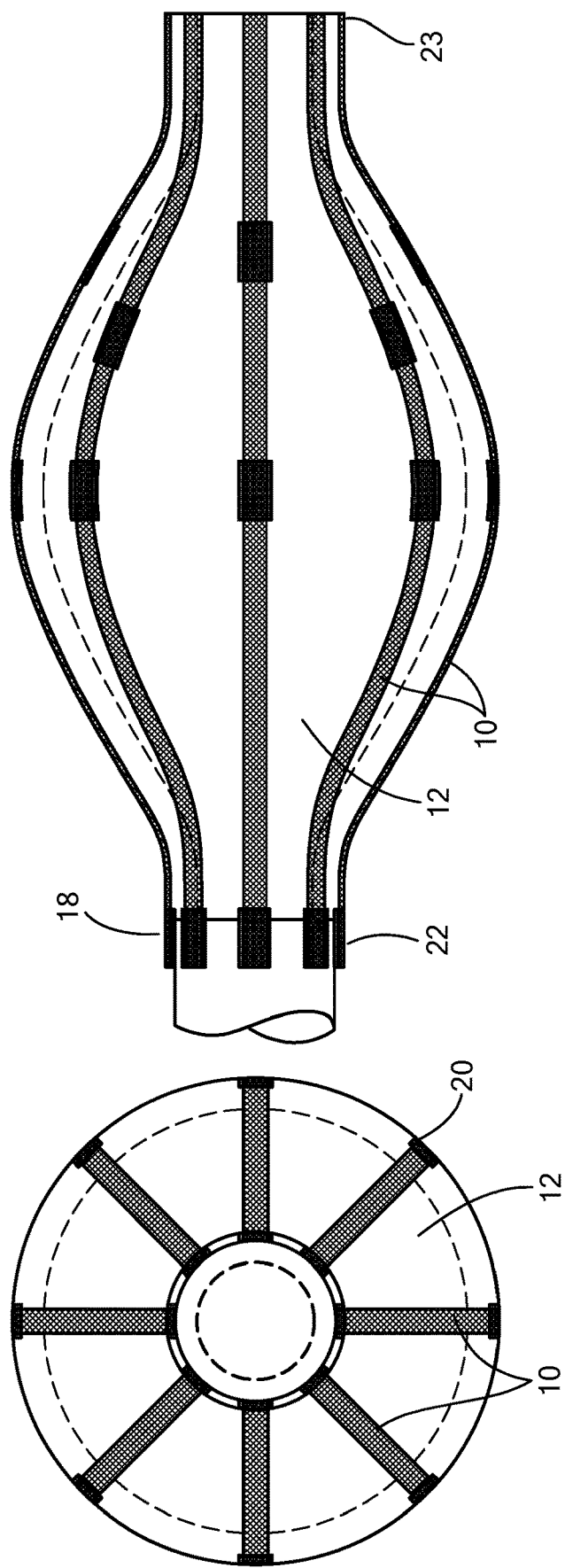
FIG. 19 shows a fifth step of the second exemplary method of forming the balloon, in which the polymeric material at the ends of the balloon is modified or removed to allow for electrical connection to other components of the medical device.
FIG. 20 shows a cross-sectional view of the polymeric material of FIG. 19.

In a fifth step, as shown in FIGS. 19 and 20, a chemical process may be used to remove a layer of the polymeric material 12 in specific desired locations. As a non-limiting example, a chemical may be used on the polymeric material 12 to remove at least a portion polymeric material 12 so that the electrically conductive material 10 may be exposed at certain desired locations. This will allow a portion of the catheter apparatus, such as a braid wire to be connected to the electrically conductive material 10. This can give greater access to electrically conductive material so that different parts of the catheter may be connected with the electrically conductive material 10 and/or the polymeric material. The mandrel 23 may be used to structurally support the polymeric material 12 and the electrically conductive material 10 during this process.

Figure 21:
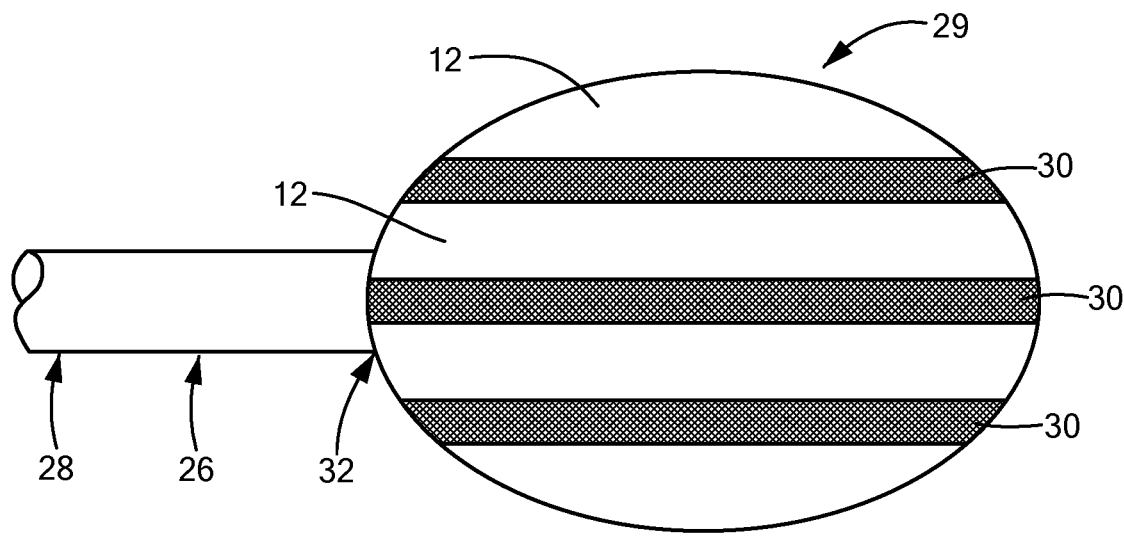
FIG. 21 shows a first exemplary embodiment of a medical device having a balloon with electrically conductive elements.
Figure 22:
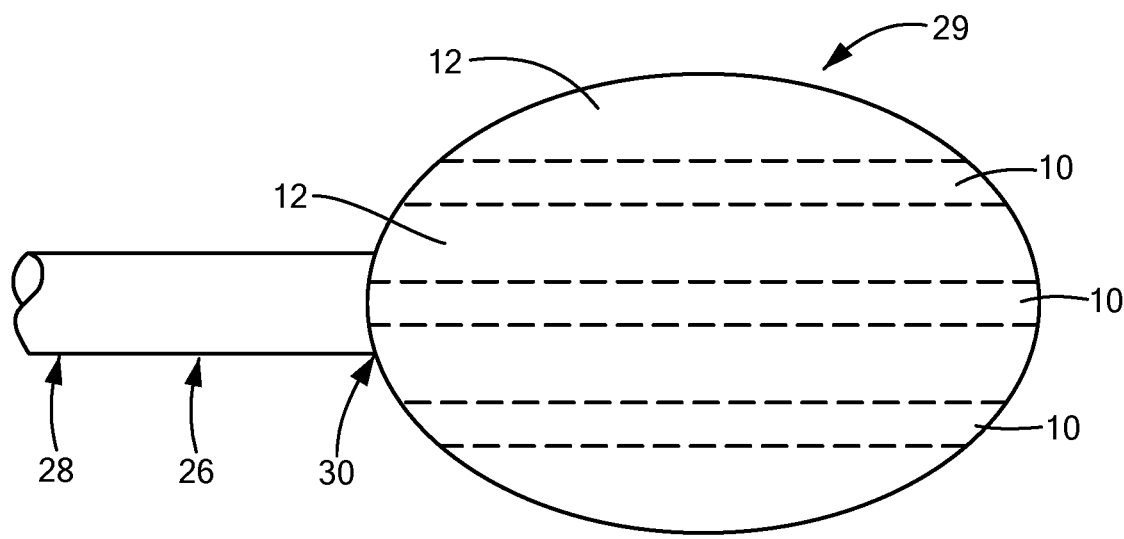
FIG. 22 shows a second exemplary embodiment of a medical device having a balloon with electrically conductive elements.

Exemplary embodiments of a medical device 29 having a balloon 24 with electrically conductive material 10 are shown in FIGS. 21 and 22. In a first embodiment as shown in FIG. 21, there is a balloon 24 composed of an electrically insulative polymeric material 12 with electrically conductive elements 30. The electrically conductive elements 30 may be discrete deposits of electrically conductive material 10. The electrically conductive elements 30 may be on the surface of the balloon 24 or they may be embedded within the balloon 24. The outer surface of the balloon 24 may include an elongate body 26 having a proximal portion 28 and a distal portion 30, the balloon 24 being coupled to the distal portion 30. The elongate body 26 may be connected to other elements of the catheter.

In the second embodiment of the device as shown in FIG. 22, the dotted surface shows the embedded electrically conductive elements 30 after the outer surface of the balloon 24 has been removed. The embedded electrically conductive elements 30 may include an embedded first electrically conductive element 30. At least a portion of the embedded electrically conductive elements 30 may be exposed with an electroplated layer of a second electrically conductive element 30. In alternative embodiments, there may be various layers of embedded electrically conductive elements 10 in the balloon 24. The embedded electrically conductive elements 30 may include graphene nanotubes or gold particles that have been supersonically implanted into the polymeric material 12. If the electrically conductive elements 30 are embedded within the balloon 24, at least a portion of the polymeric material 12 may be removed from the outer surface of the balloon 24 to expose at least a portion of the embedded electrically conductive elements 30. This removal process may include, but is not limited to the chemical process and ablation.

Figure 23:
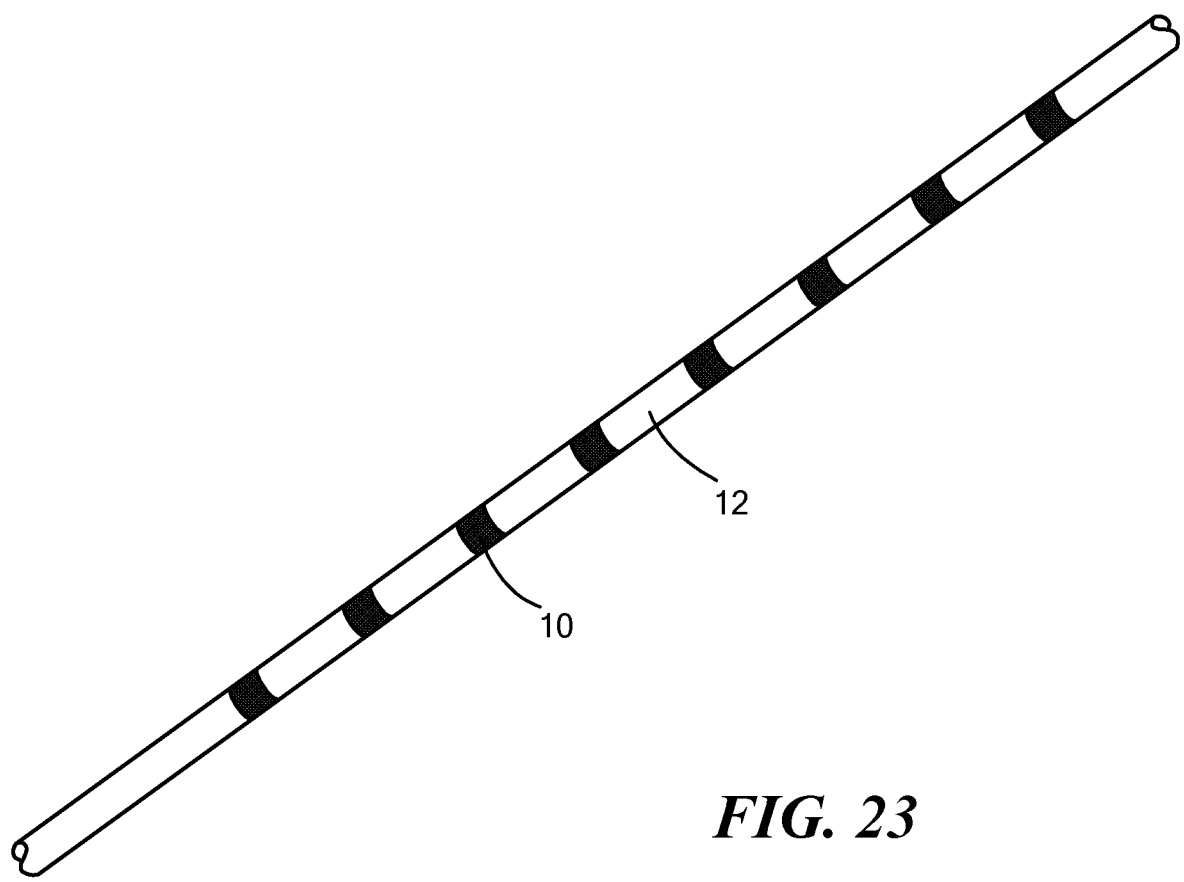
FIG. 23 shows a medical device formed by a third exemplary method, the method including depositing electrically conductive material onto at least a portion of an elongate body.
Figure 24:
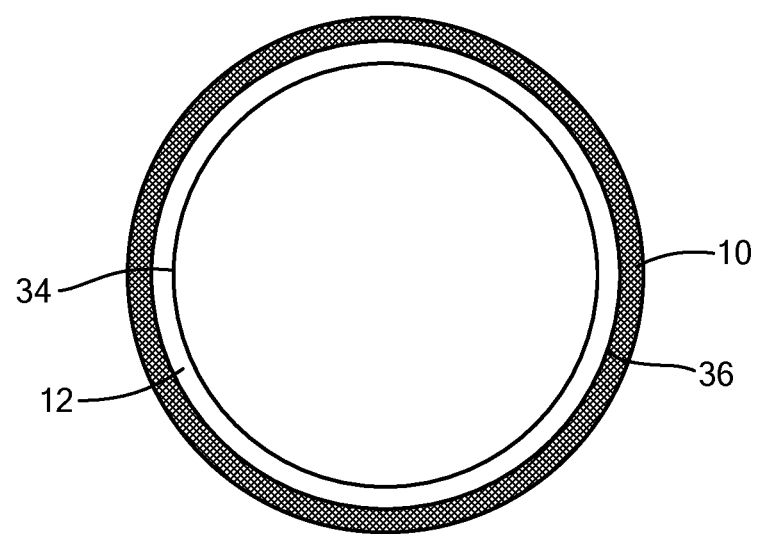
FIG. 24 shows a cross-sectional view of the elongate body of FIG. 21.

Referring now to FIGS. 23 and 24, a third exemplary method of forming a linear medical device is shown. In this exemplary method, the conductive material 10 may be printed on the polymeric material 12. The polymeric material 12 may be in a tubular configuration that is not expandable with an interior surface 34 and an exterior surface 36. The conductive material may be printed onto the exterior surface 36 of the polymeric material 12. Alternatively, the conductive material 10 may also be printed onto the interior surface 34. The printing may be done in various shapes and sizes, depending upon the amount of conductive material 10 to be printed onto the polymeric material 12. As a non-limiting example, the conductive material 10 may be printed in a ring shape around the tubular configuration of the polymeric material 12. The polymeric material 12 may include thermoplastic polymer, such as polyether block amide.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings without departing from the scope of the following claims.

What is claimed is:

1. A method of manufacturing a balloon with electrically conductive material, the method comprising:
    extruding a polymeric material to form the balloon, the polymeric material including embedded electrically conductive material; and
    removing at least a portion of the polymeric material forming the balloon to expose at least a portion of the embedded electrically conductive material.

2. The method of claim 1, wherein the polymeric material is at least one of a group consisting of a thermoplastic polyurethane, a thermoplastic elastomer, a polyamide, an ethylene vinyl acetate, a polyvinylidene fluoride, and a polyvinyl chloride.

3. The method of claim 1, wherein the electrically conductive material is an embedded first electrically conductive material, the method further comprising electroplating the exposed at least a portion of the embedded first electrically conductive material with a second electrically conductive material.

4. The method of claim 3, wherein the embedded first electrically conductive material is a conductive ink and the second electrically conductive material is gold.

5. The method of claim 1, wherein the extruded polymeric material has a tubular first configuration, the method further comprising:
    expanding the polymeric material into an expanded second configuration.

6. The method of claim 5, wherein the at least a portion of the polymeric material is removed to expose at least a portion of the embedded electrically conductive material after the polymeric material is expanded into the expanded second configuration.

7. The method of claim 1, wherein the electrically conductive material is a temperature-activated material, the method further comprising:
    heating the electrically conductive material, the conductive material becoming conductive when heated.

8. The method of claim 1, wherein the electrically conductive material includes flakes of electrically conductive material.

9. The method of claim 1, wherein the electrically conductive material includes nanotubes.

10. The method of claim 9, wherein the nanotubes are at least one of a single wall carbon nanotube and a single wall graphene nanotube.

11. The method of claim 1, wherein the electrically conductive material includes at least one nanowire.

12. The method of claim 11, wherein the at least one nanowire includes at least one silver nanowire.

13. The method of claim 1, wherein the embedded electrically conductive material is supersonically implanted into the polymeric material as the polymeric material is extruded.

* * * * *